US008658157B2

(12) United States Patent
Mollstam et al.

(10) Patent No.: US 8,658,157 B2
(45) Date of Patent: *Feb. 25, 2014

(54) SELECTION AND USE OF LACTIC ACID BACTERIA FOR REDUCING DENTAL CARIES AND BACTERIA CAUSING DENTAL CARIES

(71) Applicants: Bo Mollstam, Lerum (SE); Eamonn Connolly, Lidingo (SE)

(72) Inventors: Bo Mollstam, Lerum (SE); Eamonn Connolly, Lidingo (SE)

(73) Assignee: Biogaia AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/668,624

(22) Filed: Nov. 5, 2012

(65) Prior Publication Data

US 2013/0121932 A1    May 16, 2013

Related U.S. Application Data

(60) Division of application No. 12/287,918, filed on Oct. 15, 2008, now Pat. No. 8,343,483, which is a division of application No. 10/869,185, filed on Jun. 14, 2004, now Pat. No. 7,517,681, which is a continuation-in-part of application No. 10/353,407, filed on Jan. 29, 2003, now Pat. No. 6,872,565.

(51) Int. Cl.
| | |
|---|---|
| *A22C 13/00* | (2006.01) |
| *A23C 9/12* | (2006.01) |
| *A23C 9/154* | (2006.01) |
| *A23C 21/00* | (2006.01) |
| *A01N 63/00* | (2006.01) |

(52) U.S. Cl.
USPC .......... 424/93.45; 426/34; 426/390; 426/580; 426/583; 435/252.9; 435/853

(58) Field of Classification Search
None
See application file for complete search history.

(56) References Cited

U.S. PATENT DOCUMENTS

| | | |
|---|---|---|
| 5,413,960 A | 5/1995 | Dobrogosz |
| 5,439,678 A | 8/1995 | Dobrogosz |
| 5,800,813 A | 9/1998 | Casas |
| 5,837,238 A | 11/1998 | Casas |
| 5,849,289 A | 12/1998 | Dobrogosz |
| 6,036,952 A | 3/2000 | Oh |
| 6,100,388 A | 8/2000 | Casas |
| 6,103,227 A | 8/2000 | Wolf |
| 6,461,607 B1 | 10/2002 | Farmer |
| 6,835,397 B2 | 12/2004 | Lee et al. |

FOREIGN PATENT DOCUMENTS

| | | |
|---|---|---|
| WO | PCT/FR92/00126 | 9/1992 |
| WO | PCT/EP00/07919 | 3/2001 |

OTHER PUBLICATIONS

Babaahmady, Efficiency of *Lactobacillus rhamnosus* GG against dental caries, Yogurts, Jun. 2002.
Fitzgerald, Cariogenicity of two strains of human oral *Lactobacilli*, J. Dent. 59(5):832-7, 1980.
Jacques, Characterization of two strains of cariogenic *Lactobacilli*, J. Gen.Microbiol. 118:283-6, 1980.
Nase, Effect of long-term consumpton of a probiotic bacterium, *Lactobacillus rhamnosus* GG, in milk on dental caries and caries risk in children. Caries Res. 35(6):412-20, 2001.

*Primary Examiner* — Debbie K Ware
(74) *Attorney, Agent, or Firm* — Lynn E. Barber

(57) ABSTRACT

New strains of *Lactobacillus* that have been selected for their capability of improved reduction the number of *Streptococcus mutans* in the mouth of mammals through inhibiting activity in combination with better binding to the oral mucins and dental plaque, thereby preventing, reducing or treating dental caries, and products derived from said strains, including agents for treatment or prophylaxis of caries for administration to humans.

8 Claims, No Drawings

SELECTION AND USE OF LACTIC ACID BACTERIA FOR REDUCING DENTAL CARIES AND BACTERIA CAUSING DENTAL CARIES

CROSS-REFERENCE TO RELATED APPLICATIONS

This is a divisional application of application of U.S. patent application Ser. No. 12/287,918 filed Oct. 15, 2008, now U.S. Pat. No. 8,343,483, which is a divisional application of U.S. patent application Ser. No. 10/869,185 filed Jun. 14, 2004, now U.S. Pat. No. 7,517,681, issued Apr. 14, 2009, which is a continuation-in-part of U.S. patent application Ser. No. 10/353,407 filed Jan. 29, 2003 now U.S. Pat. No. 6,872,565, issued Mar. 29, 2005, the disclosure of which is incorporated herein by reference.

BACKGROUND OF THE INVENTION

1. Field of the Invention

This invention relates to use of nonpathogenic anti-cariogenic lactic acid bacteria strains, and products and methods using such strains, mutants, metabolites and components thereof for treatment and prophylaxis of dental caries caused by oral bacteria such as *Streptococcus mutans*, and other caries-causing pathogens.

2. Description of the Related Art

The oral cavity of humans and other mammals contains many different species of bacteria, including a number of different species of *Lactobacillus*. Caries is a disease caused by bacteria. Already in 1890, Miller in "Chemico-Parasitic Theory" presented the hypothesis that caries is caused by oral bacteria producing acids from digestive carbohydrates, which will dissolve the hydroxyhepatite of the teeth. It was later confirmed in gnotobiotic rats, for example, that normal oral bacterial flora, primarily of the mutans streptococci group and secondarily the lactobacilli group are involved in caries production. These "acidogenic" species resident in the oral cavity are associated with the presence and onset of dental caries (Locsche W J, Microbioiog Rev., 1986:50:353-380). There are seven bacterial species within the group mutans streptococci, where *Streptococci mutans* (serotype c,e,f) are found in 90% of all human isolates (Under L., Oral Mikrobiologi 1996, ISBN 91-7205-037-3). There is abundant evidence that the initiation of caries requires a relatively high proportion of *S. mutans* within dental plaque. These bacteria adhere well to the tooth surface, produce higher amounts of acid from sugars than other bacterial types, can survive better than other bacteria in an acid environment, and produce extracellular polysaccharides from sucrose. When the proportion of *S. mutans* in plaque is high (in the range 2-10%) a patient is at high risk for caries. When the proportion is low (less than 0.1%) the patient is at low risk. Because they are more acid tolerant than other bacteria, acid conditions within plaque favor the survival and reproduction of mutans streptococci.

Two other types of bacteria are also associated with the progression of caries through dentin. These are several species of *Lactobacillus*, and *Actinomyces viscosus*. These bacteria are also highly acidogenic and survive well in acid conditions. The involvement of *Lactobacillus* in dental, caries has been established (Smith et al., Microbios 105: 77-85, 2001). In fact, estimation of the lactobaeillus counts in saliva, in addition to the estimation of mutans streptococci counts, using different selective media or other techniques, has been used, for many years as a "caries test" and as a way to attempt to identify groups at high risk for caries. Thus, *Lactobacillus* strains, some isolated from human dental plaque, may be highly cariogenic (Fitzgerald et al, J. Dent. Res. 60: 919-926, 1981).

For a bacteria to be a primary pathogen in the formation of dental caries it is required that it have a combination of several of the required characteristics (Linder, 1996): ability to adhere and colonize on the teeth surface; ability to accumulate in large numbers on a limited surface of the teeth; ability to quickly produce acid from carbohydrates found in foods; and ability to continue acid production even under low pH in the dental plaque.

Dietary sucrose changes both the thickness and the chemical nature of plaque. Mutans streptococci and some other plaque bacteria use the monosaccharide components (glucose and fructose) and the energy of the disaccharide bond of sucrose to assemble extracellular polysaccharides. These increase the thickness of plaque substantially, and also change the chemical nature of its extracellular space from liquid to gel. The gel limits movement of some ions. Thick, gel-plaque allows the development of an acid environment against the tooth surface, protected from salivary buffering. Plaque that has not had contact with sucrose is both thinner and better buffered. A diet with a high proportion of sucrose therefore increases caries risk. Thicker plaque occurs in pits and fissures and, in patients with poor oral hygiene, near the gingival margin.

Given this concept of the nature of the disease, it is clear that prevention and treatment of dental caries requires hindering the effects of *S. mutans*, for example, through dietary change as means of reducing the substrate for the bacteria, to reinforce the surface structure of the teeth or reduction of the number of *S. mutans* bacteria. Thus, treatments that have been tried include: efforts at changing the microflora, using agents such as topical chlorhexidine and topical fluoride; reducing the amount of dietary sucrose, by dietary change and substitution for sweeteners more difficult to metabolize by *S. mutans*, such as Sorbitol, Aspartan, Xylitol; decreasing the frequency of eating, by dietary choice; adding fluoride, particularly through daily application during tooth brushing; and increasing salivary flow, using mechanical stimulation during vigorous chewing to enhance flow, by changing drugs which reduce flow, or by using drugs to enhance flow. Different approaches has been evaluated for preventing dental caries, for example, one composition uses a lytic enzyme produced by a bacteriophage specific for *Streptococcus mutans* (U.S. Pat. No. 6,399,098 of Fischetti et al.). Also, a strain of *Lactobacillus zeae* has been modified through genetical engineering to produce van antibody on its surface to neutralize the detrimental streptococcal bacteria, (Hammarstrom L., July 2002 issue of Nature Biotechnology); however this approach with genetically modified organisms faces an unknown safety approval situation.

In addition, one strain of *Lactobacillus rhamnosus* (ATCC 53013, strain GG) has been promoted as a probiotic method of reducing *Streptococcus sabrimus* and mutans streptococci generally (Nase et al. Caries Res. 35: 412-420, 2001). Further work showed that use of this strain as a starter in fermenting milk did not influence the titer of antibodies against human cariogenic bacteria that were present in the milk (Wei et al., Oral Microbio. & Immunol. 17: 9-15, 2002). *L. rhamnosus* GG differs from *L. reuteri* in many ways, including fermentation characteristics and isolation source. Other microorganisms that have been found to have inhibitory activity against the formation of dental plaque include *Enterococcus, Lactobacillus acidophilus* V20, and *Lactobacillus lactis* 1370 (Oh, U.S. Pat. No. 6,036,952). In order to inhibit *S. mutans*, other work has been done using so called "competitive exclusion"

concepts. For example, *L. reuteri* strain ATCC 55730 has been shown to inhibit *S. mutans* (Nikawa H. et al. News release by Hiroshima University Jul. 11, 2002). A tablet product which is on the market in Japan called LS1, containing a strain of *Lactobacillus salivarius* (LS1) (by Frente Ltd. Japan) is claimed to inhibit *S. mutans*.

Strains of a wide variety of *Lactobacillus* species, including *Lactobacillus reuteri*, have been used in probiotic formulations. *Lactobacillus reuteri* is one of the naturally occurring inhabitants of the gastrointestinal tract of animals, and is routinely found in the intestines, and occasionally in the birth channel, breast milk and mouth of healthy animals, including humans. It is known to have antibacterial activity. See, for example, U.S. Pat. Nos. 5,439,678, 5,458,875, 5,534,253, 5,837,238, and 5,849,289. When *L. reuteri* cells are grown under anaerobic conditions in the presence of glycerol, they produce the antimicrobial substance known as reuterin (β-hydroxy-propionaldehyde). Other antimicrobial substances beside the traditional organic acids have also been reported such as "Reutericyclin" (Höltzel, A. et al. Angewandte Chemie International Edition 39, 2766-2768, 2000) and "PCA (pyroglutamic acid)" (Yang, Z. Dissertation, Univ. of Helsinki, March 2000), and "Reutericin 6" (Toba T, et al., Lett Appl Microbiol 13: 281-6.). Lactobacilli, including *L. reuteri*, are also well known to have the ability to inhibit other organisms such as *S. mutans* through local competition of nutrients and other metabolic interactions.

Mucin binding proteins of *L. reuteri* have been isolated and described. See, for example, U.S. Pat. No. 6,100,388. *Lactobacillus* strains have been reported to adhere to various cell lines and host mucus. This has been speculated to be important for probiotic activity and is derived from the concept of virulence factors in pathogenic bacteria, where vast arrays of such interactions have been discovered during the last decades (Klemm, P. and Schembri, M. A. (2000) Bacterial adhesins: function and structure. Int. J. Med. Microbiol. 290, 27-35.) It has however not been so well known that there are important differences between a *Lactobacillus* strains ability to adhere to oral mucin and mucin from other sources, Some strains are good at adhering to both oral mucin and other mucin, for example gastric mucin, others are only good at adhering to gastric mucin but less good to oral mucin, others does not adhere well to any kind of mucin. It is therefore a part of the selection method of this invention to use oral mucin to find the best strains.

While the possibility of effective antibacterial activity and some binding characteristics by *L. reuteri* is known, and *S. mutans* inhibiting effects of *L. reuteri* strain ATCC 55730 and *Lactobacillus* GG ATCC 53103 are also known, and some other lactic acid bacteria have been claimed to be anti-cariogenic, it was not previously known that substantial differences existed between lactobacilli strains in their ability to reduce the number of *Streptococci mutans* in the oral cavity and thereby caries, nor that such strains could be selected.

It is therefore an object of the invention to provide better strains of *Lactobacillus* which have been selected for their capability to reduce the number of *S. mutans* in the mouth through antimicrobial activity in combination with good capabilities of adhering to oral mucin and thereby successfully prevent, reduce or treat dental caries, it is a further object of the invention to provide products containing said strains, mutants, metabolites or components thereof, including agents for prophylaxis or treatment of caries associated with *S. mutans* for administration to humans.

Other objects and advantages will be more fully apparent from the following disclosure and appended claims.

SUMMARY OF THE INVENTION

The invention herein comprises strains of *Lactobacillus* that have been selected for their capability of reducing the number of *Streptococcus mutans* in the mouth of mammals through inhibiting activity, including mutants, metabolites and components thereof, in combination with good binding of the *Lactobacillus* to oral mucin and dental plaque for preventing, reducing or treating dental caries, and products derived from said strains, including agents for treatment or prophylaxis of caries for administration to humans.

Other objects and features of the inventions will be more fully apparent from the following disclosure and appended claims.

DETAILED DESCRIPTION OF THE INVENTION AND PREFERRED EMBODIMENTS THEREOF

The present invention provides a product, for inhibiting the growth and activity of dental caries bacteria, comprising cells or metabolites or components of at least one selected strain of *Lactobacillus* with good antimicrobial activity against *Streptococcus mutans* and good binding characteristics to oral mucin and thereby prevent, reduce or treat dental caries. Such strains includes *L. reuteri* CF2-7F (ATCC PTA-4965), *L. reuteri* MF2-3 (ATCC PTA-4964) and especially *L. reuteri* FJ1 "Prodentis" (ATCC PTA-5289) and *L. reuteri* FJ3 (ATCC PTA-5290). These strains are available to the public under the Budapest Treaty at the American Type Culture Collection (Rockville, Md.) the last two having been deposited there on Jul. 25, 2003. All restrictions upon availability to the public will be irrevocably removed upon granting of the patent.

In the selection method used herein, the inhibiting effects of *Streptococci mutans* are examined by traditional microbiological methods with the bacterial cells as well as separately analyzing inhibition by secreted metabolites and components in the supernatant of the grown test strains, measured by a method of determining the ATP (adenosine triphosphate) level of *Streptococcus mutans* which correlates well with the total cell volume of viable *S. mutans* cells. (ref. Nikawa H. et al. Journal of Dentistery, Vol 26, No 1, pp. 31-37, 1998). The adhesion capabilities are measured using oral mucin coated in microtiter wells (ref. Jonsson et al. 2001 FEMS Microbiol. lett. 204: 19-22). The reason for also testing inhibition and adhesion by secreted metabolites and cell components is that the present invention also could be used with non-viable cells or parts of dead cells fulfilling the selection criteria.

The details of this will be more clearly understood from the Examples.

The product of the invention can be any product for placement in the mouth as a preventative or treatment for dental caries, or for nutritional or breath purpose, such as food products, dental treatment products such as mouthwashes or other specified health products, chewing gum lozenges and the like. Food products lending them selves particularly to use in the invention include milk-containing products such as yogurt, and also juices, drinks and the like. The dental treatment products that may be used in the invention include toothpastes, liquid tooth cleansers, mouthwashes, anti-halitosis products, and the like.

The concentration of selected *Lactobacillus* cells or metabolites or components thereof, needed for effectiveness of a product of the invention depends on the type of food and the amount of food to be ingested (or the time of use in the mouth of a non-food dental treatment product), but it is usually preferable to have equivalent of about $10^5$-$10^8$ CFU (colony-forming units) or more per daily intake of a product. Amounts up to about $10^{10}$-$10^{11}$ CFU are possible and can be used to increase efficacy without adversely affecting the product's organoleptic characteristics (its flavor or smell). When the product is yogurt or other lactic acid fermentation product, the lactic acid fermentation strain(s) used to produce the product would preferably be standard cultures for this particular purpose, and the anti-cariogenic bacteria, or metabolites or components thereof, of the invention may be added either before or after the fermentation of the product at a level equivalent of about $10^6$-$10^8$ CFU per daily serving of yogurt or more as discussed above.

Preferably the product of the invention does not contain other antibacterial components, at least none that inhibit or kill selected *Lactobacillus* strain(s), or metabolites or components thereof, or interfere with its anti-cariogenic activity.

The strain(s) of *Lactobacillus*, or metabolites or components thereof, can be an additive mixed into the ingredients or kneaded into or coated on the product by means known in the art for formulation of products of that type. When using cells and if preparation of the selected food or other product of the invention requires a heating step, the *Lactobacillus* strain(s) should be added after the heating. Once the selected *Lactobacillus* cells are in the product, it is preferred not to heat the product to 60-70 degrees C. or above for a longer period of time.

The features of the present invention will be more clearly understood by reference to the following examples, which are not to be construed as limiting the invention.

Example 1

Method of Selection of Strains

The selection of the *Lactobacillus* strains to be used according to this invention can be done in the following three step manner:

a) Evaluation of Inhibiting Effect of *S. mutans* by Cells of *Lactobacillus* Strains An example of a strain to use to measure the inhibitory effect is *Streptococcus mutans*, ATCC25175 (available from The American Type Culture Collection, Manassas, Va., USA). The isolate is grown in trypticase soy broth (Difco, Detroit, USA) supplemented with 0.5% yeast extract (Difco) (TSBY). The cells are harvested during the exponential growth phase by centrifugation at 1000×g, washed twice with PBS and resuspended in the same buffer. The cell suspensions are subjected to a low-intensity ultrasonic device to disperse bacterial aggregates.

The test *Lactobacillus* strain is grown in MRS broth (Difco), and harvested during the exponential growth phase by centrifugation at 1000×g, washed twice with phosphate buffered saline (PBS; pH 6.8) and re-suspended in the same buffer.

The optical densities of the bacterial suspensions are measured in a 1.0 ml cuvette with a 1 cm light path, and the suspensions are adjusted to a final concentration of $1.0 \times 10^8$ CFU (colony forming unit)/ml.

The inhibitory assay is conducted as follows, the suspension of *S. mutans* and the suspension of *Lactobacillus* are mixed in the ratios of 100-0, 75-25, 50-50 and 25-75 in sterile centrifugation tube (total volume 100 µL), added the BHI broth up to 10 ml, vortex mixed for ten seconds and incubated for 90 min at 37° C. with gentle shaking. As a control, the suspension of *S. mutans* is mixed with an equal volume of PBS in the control tubes (free of *Lactobacillus*). Afterwards each suspension is washed by centrifugation at 1000×g, washed twice with PBS, and plated on MS agar to determine the CFU count of *S. mutans*. The % survival of *S. mutans* is obtained from following formula.

$$\% \text{ survival of } S. \text{ mutans} = \frac{CFU \text{ of } S. \text{ mutans incubated with } Lactobacillus \times 100}{CFU \text{ of } S. \text{ mutans incubated with } PBS}$$

The assay should be carried out with minimum triplicate samples. All the numerical data obtained should be statistically analyzed.

b) Evaluation of Inhibiting Effect of *S. mutans* by Metabolites or Components of *Lactobacillus* Strains Also used here as an example of a strain to use to measure the inhibitory effect is *Streptococcus mutans*, ATCC25175 (available from The American Type Culture Collection, Manassas, Va., USA). The isolate is grown in trypticase soy broth (Difco, Detroit, USA) supplemented with 0.5% yeast extract (Difco) (TSBY). The cells are harvested during the exponential growth phase by centrifugation at 1000×g, washed twice with PBS and resuspended in the same buffer. The cell suspensions are subjected to a low-intensity ultrasonic device to disperse bacterial aggregates and adjusted to final concentration of $10^8$ CFU/mL.

The test *Lactobacillus* strain is grown in MRS broth (Difco), harvested during the exponential growth phase by centrifugation at 1000×g, washed twice with phosphate buffered saline (PBS; pH 6.8) and re-suspended in the same buffer.

The optical densities of the bacterial suspensions are measured in a 1.0 ml cuvette with a 1 cm light path, and the suspensions is adjusted to a final concentration of $1.0 \times 10^8$ CFU/ml. 100 µL of the lactobacilli suspension was added to 2.0 mL of MRS broth, and incubated at 37° C. for 48 h with reciprocal shaking (120 rpm). After the incubation, the *lactobacillus* cells where removed by centrifugation, and the resulting supernatant was filtered (pore size 0.25 µm).

The inhibitory assay was conducted as follows. 100 µL of the suspension of *S. mutans* was added to 1.0 mL of TSBY and 1.0 mL of the supernatants of each tested strain of lactobacilli was mixed, and incubated for 24 h in 37° C. with reciprocal shaking (120 rpm). As a control the suspension of *S. mutans* was mixed with equal volume of MRS in the control tubes (free of supernatants from lactobacilli). Afterwards each suspension was washed by centrifugation at 1000×g washed twice with PBS and the amount of adenosine triphosphate of grown *S. mutans* was determined using the method described in; Nikawa. H. et al. Journal of Dentistery, Vol 26, No 1, pp. 31-37, 1998.

C) Evaluation of Adhesion Capabilities to Oral Mucin of *Lactobacillus* Strains

The *Lactobacillus* strains to be tested are collected. The bacteria are grown at 37° C. in MRS broth (Difco) for 16 h. Plates are incubated in anaerobic jars under $CO_2+N_2$ atmosphere (GasPak System, BBL, Becton Dickinson Microbiology Systems, Cockeysville, Md., USA).

Oral mucus as human saliva are collected, centrifuged, sterile filtered and coated into microtiter wells as described. The mucus are collected in 200 ml ice-cold phosphate-buffered saline (PBS) (8.0 g NaCl, 0.2 g KCl, 1.44 g $Na_2HPO_4 \cdot 2H_2O$ and 0.2 g $KH_2PO_4$ per 1000 ml of $dH_2O$) and supplemented with 0.05% Tween 20 (PBST). The resulting suspension is centrifuged first at 11000 g for 10 min and then at 26000 g for 15 min in order to remove cells and particulate matter. As an alternative gastric mucin is (Sigma, M1778) used. The crude mucus preparation is stored at 20° C. The mucus material is diluted to approximately 100 µg ml-1 in 50 mM Na2CO3 buffer, pH 9.7 and incubated overnight in microtiter wells (Greiner) (150 µl per well) at 4° C. with slow rotation. The wells are blocked with PBS with 1% Tween 20 for 1 h and thereafter washed with PBST. Wells coated with BSA are used as controls.

The strains to be tested are grown as per above, washed once in phosphate-buffered saline (PBS) (pH 7.3) supplemented with 0.05% Tween 20 (PBST) and diluted to $OD_{600}$ in the same buffer. One hundred microliters bacterial suspension is added to each well and incubated over night at 4° C. The wells are washed 4 times with PBST and binding examined with an inverted microscope. The buffer is poured off and, after the wells had dried, the binding is measured over the whole surface of the well in a BioRad Gel Doe 2000 instrument (BioRad Laboratories, Herkules, Calif., USA). All measurements are done in triplicate.

The *Lactobacillus* strains showing best results in both inhibiting of *S. mutans* using *Lactobacillus* cells and inhibiting *S. mutans* using metabolites and components of said *Lactobacillus* as well as best results in adhesion to oral mucin according to the assays, are selected.

Example 2

Selection of Strains

1. *L. reuteri* SD2112 (ATCC 55730)
2. *L. reuteri* DSM 20016 (DSM 20016)
3. *L. reuteri* MM2-3 (ATCC PTA-4659)
4. *L. reuteri* CF2-7F (ATCC PTA-4965)
5. *L. reuteri* MF2-3 (ATCC PTA-4964)
6. *L. reuteri* MF14-C (Culture collection of Biogaia AB, Raleigh N.C., USA)
7. *L. reuteri* MF52-1F (Culture collection of Biogaia AB, Raleigh N.C., USA)
8. *L. reuteri* MM7 (Culture collection of Biogaia AB, Raleigh N.C., USA)
9. *L. reuteri* FJ1, "Prodentis" (ATCC PTA-5289)
10. *L. reuteri* FJ3 (ATCC PTA-5290).
11. *L. salivarus* LS1 (isolated from the LS1 tablet by Frente Ltd. Japan)
12. *L. rhamnosus* GG (ATCC 53103)

In this study the above listed *Lactobacillus* strains are chosen to be evaluated using the selection criteria of inhibition of *S. mutans* and adhesion to oral mucin, the methods set forth in Example 1 are used. The *Lactobacillus* strains showing best results in both inhibiting of *S. mutans* using *Lactobacillus* cells and inhibiting *S. mutans* using metabolites and components of said *Lactobacillus* as well as best results in adhesion to oral mucin according to the assays, are selected. Results of inhibition are shown in Table 1, and results of adhesion are shown in Table 2.

TABLE 1

Inhibition of *S. mutans* of *Lactobacillus* strains as cells as well as with supernatants of said *Lactobacillus* according to the described assays.

| Strain | CFU/g survival *S. mutans* ratio 10:1 | CFU/g survival *S. mutans* ratio 3:1 | CFU/g survival *S. mutans* ratio 1:1 | pmol/L ATP amount of *S. mutans* in supern. assay | Selection to next step |
|---|---|---|---|---|---|
| *L. reuteri* SD2112 | 2.0E+08 | 8.0E+07 | 6.0E+07 | 94644.9 | — |
| *L. reuteri* DSM 20016 | 1.0E+08 | 2.0E+07 | 7.0E+06 | 479.1 | S |
| *L. reuteri* MM2-3 | 1.0E+08 | 7.0E+07 | 5.0E+07 | 35125.3 | — |
| *L. reuteri* CF2-7F | 1.0E+08 | 1.0E+07 | 7.0E+05 | 438.6 | S |
| *L. reuteri* MF2-3 | 2.0E+08 | 2.0E+07 | 4.0E+06 | 33158.8 | S |
| *L. reuteri* MF14-C | 9.0E+07 | 8.0E+07 | 7.0E+07 | 29644.3 | — |
| *L. reuteri* MF52-1F | 1.0E+08 | 8.0E+07 | 7.0E+07 | 3120.7 | — |
| *L. reuteri* MM7 | 2.0E+08 | 8.0E+07 | 7.0E+07 | 100110.0 | — |
| *L. reuteri* FJ1 | 1.0E+08 | 4.0E+06 | 7.0E+04 | 3374.3 | S |
| *L. reuteri* FJ3 | 1.0E+08 | 1.0E+07 | 4.0E+05 | 11364.1 | S |
| *L. salivarius* LS1 | 1.0E+08 | 8.0E+08 | 7.0E+09 | 502.8 | — |
| *L. rhamnosus* GG | 2.0E+08 | 8.0E+07 | 7.0E+07 | 16113.2 | — |

(S = selected)

TABLE 2

Adhesion of *Lactobacillus* strains according to the described assays.

| Strain | $ODxmm^2$ Gastric mucin | $ODxmm^2$ Oral mucin | Selection this step | Selection earlier step | Final selection |
|---|---|---|---|---|---|
| *L. reuteri* SD2112 | 0.39 | 0.78 | — | — | — |
| *L. reuteri* DSM 20016 | 9.42 | 7.85 | S | S | FS |
| *L. reuteri* MM2-3 | 11.6 | 3.55 | S | — | — |
| *L. reuteri* CF2-7F | 11.73 | 5.77 | S | S | FS |
| *L. reuteri* MF2-3 | 6.04 | 2.82 | S | S | FS |
| *L. reuteri* MF14-C | 0.2 | 0.17 | — | — | — |
| *L. reuteri* MF52-1F | 0.94 | 1.45 | — | — | — |
| *L. reuteri* MM7 | 0.39 | 2.14 | — | — | — |
| *L. reuteri* FJ1 | 7.51 | 2.77 | S | S | FS |
| *L. reuteri* FJ3 | 7.11 | 5.9 | S | S | FS |
| *L. salivarius* LS1 | 0.19 | 1.15 | — | — | — |
| *L. rhamnosus* GG | 0.5 | 0.33 | — | — | — |

(S = selected) (FS = Finally selected)

Example 3

Manufacturing of Products Containing Selected Strain

In this example, *L. reuteri* FJ1 "Prodentis" (ATCC PTA-5289), is selected based on good growth characteristics in general and favorable results in the earlier mentioned selection in Example 2 using the methods above for *S. mutans* inhibition and mucin binding, in order to add the strain to a chewing gum. The *L. reuteri* strain is grown and lyophilized, using standard methods for growing *Lactobacillus* in the industry.

The steps of an example of a manufacturing process of chewing gum containing the selected strain follow, with it being understood that excipients, fillers, flavors, encapsulators, lubricants, anticaking agents, sweeteners and other components of chewing gum products as are known in the art, may be used without affecting the efficacy of the product:

1 Melting. Melt Softisan 154 (SASOL GMBH, Bad Homburg, Germany) in a vessel and heat it to 70° C. to assure complete disruption of the crystalline structure. Then cool it down to 52-55° C. (just above its hardening point).

2 Granulation. Transfer *Lactobacillus reuteri* freeze-dried powder to a Diosna high-shear mixer/granulator, or equivalent. Add slowly during approximately 1 minute the melted Softisan 154 to the *Lactobacillus reuteri* powder. No additional massing time is required. Use chopper during the addition.

3 Wet-sieving. Immediately after the granulation, pass the granules through a 1-mm sieving net by using a Tornado mill. The sieved granulate is packed in alupouches, made out of PVC-coated aluminum foil, sealed with a heatsealer to form a pouch, together with desiccant pouch, and stored refrigerated until mixing. The granulated batch is divided for two tablet batches.

4 Mixing Mix all the ingredients in a mixer, to a homogenous blend.

5 Compression. Transfer the final blend to the hopper of a rotary tablet press and compress tablets with a total weight of 765 mg, in a Kilian compresser.

6 Bulk packaging. The chewing gums are packed in alu-bags together with a drying pouch of molecular sieve. The alu-pouch is put in a plastic bucket and stored in a cool place at least one week, before final package.

In-process controls, as is standard in the industry, are shown in the following Table 3:

TABLE 3

| IPC | Test Method | Limit | |
|---|---|---|---|
| 1 | Appearance | Clear, homogenous solution | Visually |
| 2 | Temperature | 52-55° C. | Thermometer |
| 3 | *L. reuteri* assay | | CM003 |
| 4 | Appearance | Cream colored with blue spots, convex tablets plain on both sides. | Visually |
| | Uniformity of mass | 765 mg ± 5% | Ph. Eur. |

In the example herein, the selected *L. reuteri* culture is then added as above at a level of $10^7$ CFU/gram of product, and the chewing gum used by humans as a way to prevent caries. The use of SOFTISAN™, a hydrogenated palm oil, enables the *Lactobacillus* cells to be encapsulated in fat and environmentally protected, and is another particularly unique aspect of the preferred embodiment of the invention herein.

As stated above, the product of the invention may be in forms other than chewing gum, and standard methods of preparing the underling underlying product as are known in the art are beneficially used to prepare the product of the invention including the selected *L. reuteri* culture.

While certain representative embodiments have been set forth herein, those skilled in the art will readily appreciate that modifications can be made without departing from the spirit or scope of the invention.

What is claimed is:

1. A product for inhibiting the growth of dental caries bacteria, comprising cells of at least one strain of *Lactobacillus reuteri* selected to have the ability of reducing the number of *Streptococcus mutans* in the mouth for prophylaxis or treatment of dental caries in mammals using a selection assay of inhibitory activity against *Streptococcus mutans* in combination with good binding to oral mucins.

2. A product for inhibiting the growth of dental caries bacteria, comprising the cells of at least one strain of *Lactobacillus reuteri* selected to have the ability of reducing the number of *Streptococcus mutans* in the mouth for prophylaxis or treatment of dental caries in mammals using a selection assay of inhibitory activity against *Streptococcus mutans* in combination with good binding to oral mucins, wherein the at least one strain is selected from the group consisting of: *Lactobacillus reuteri* strain FJ1 "Prodentis" (ATCC PTA-5289), and *Lactobacillus reuteri* strain FJ3 (ATCC PTA-5290).

3. The product according to claim 1, wherein the product is a food product.

4. The product according to claim 3, wherein the food product is selected from the group consisting of yogurt, jelly, pudding, chewing gum, lozenge, candy, chocolate, biscuit, cookie, cheese, juice and tea.

5. The product according to claim 3, wherein the food product is a milk-containing product.

6. The product according to claim 5, wherein the food product is yogurt.

7. The product according to claim 1, wherein the product is a dental treatment product.

8. The product according to claim 7, wherein the product is a mouthwash.

* * * * *